(12) United States Patent
Chui et al.

(10) Patent No.: US 9,061,083 B2
(45) Date of Patent: Jun. 23, 2015

(54) ULTRAVIOLET LASER STERILIZATION SYSTEM

(71) Applicant: National Cheng Kung University, Tainan (TW)

(72) Inventors: Hsiang-Chen Chui, Tainan (TW); Sean Sung-Yen Juang, Tainan (TW); Hsing-Ying Lin, Tainan (TW); Chen-Han Huang, Tainan (TW); Hua-Hsien Liao, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 14/149,214

(22) Filed: Jan. 7, 2014

(65) Prior Publication Data

US 2015/0048260 A1 Feb. 19, 2015

(30) Foreign Application Priority Data

Aug. 15, 2013 (TW) .............................. 102129288 A

(51) Int. Cl.
*A61L 2/10* (2006.01)
*G21K 5/02* (2006.01)

(52) U.S. Cl.
CPC ... *A61L 2/10* (2013.01); *G21K 5/02* (2013.01); *A61L 2202/11* (2013.01); *A61L 2202/14* (2013.01); *A61L 2202/24* (2013.01); *A61L 2209/12* (2013.01)

(58) Field of Classification Search
CPC ............ A61L 2/10; A61L 2/0082; A61L 2/08; A61L 2/081; A61L 2/087; A61L 2/088; A61L 2/16; A61L 2/28; A61L 9/16; A61L 9/205; A61L 29/041; A61L 29/085; A61L 29/08; A61L 29/14; B65B 25/008
USPC ........... 250/454.11, 455.11, 492.1; 422/1, 22, 422/24, 121, 123, 182, 40, 186.3, 2, 38, 422/400, 403, 547
See application file for complete search history.

(56) References Cited

U.S. PATENT DOCUMENTS

| | | | |
|---|---|---|---|
| 7,879,288 B2 * | 2/2011 | Brown-Skrobot et al. | 422/22 |
| 8,021,608 B2 * | 9/2011 | Brown-Skrobot et al. | 422/22 |
| 8,318,089 B2 * | 11/2012 | Brown-Skrobot et al. | 422/22 |
| 2004/0120844 A1 * | 6/2004 | Tribelsky et al. | 422/2 |
| 2005/0079096 A1 * | 4/2005 | Brown-Skrobot et al. | 422/24 |
| 2007/0102280 A1 * | 5/2007 | Hunter et al. | 204/157.15 |
| 2007/0280851 A1 * | 12/2007 | Freeman et al. | 422/1 |
| 2012/0313532 A1 * | 12/2012 | Stibich et al. | 315/150 |
| 2013/0096545 A1 * | 4/2013 | Laudenslager et al. | 606/7 |

* cited by examiner

*Primary Examiner* — David A Vanore
(74) *Attorney, Agent, or Firm* — Rosenberg, Klein & Lee

(57) ABSTRACT

The invention relates to an ultraviolet laser sterilization system, comprising an ultraviolet laser module and a scanning module. The ultraviolet laser module emits an ultraviolet laser light with a wavelength ranging from 200 nm to 280 nm. The scanning module includes a plurality of reflectors for receiving the ultraviolet laser light, and a controller for controlling rotation of the reflectors to adjust an angle of emergence of the ultraviolet laser light for sterilizing a target.

3 Claims, 1 Drawing Sheet

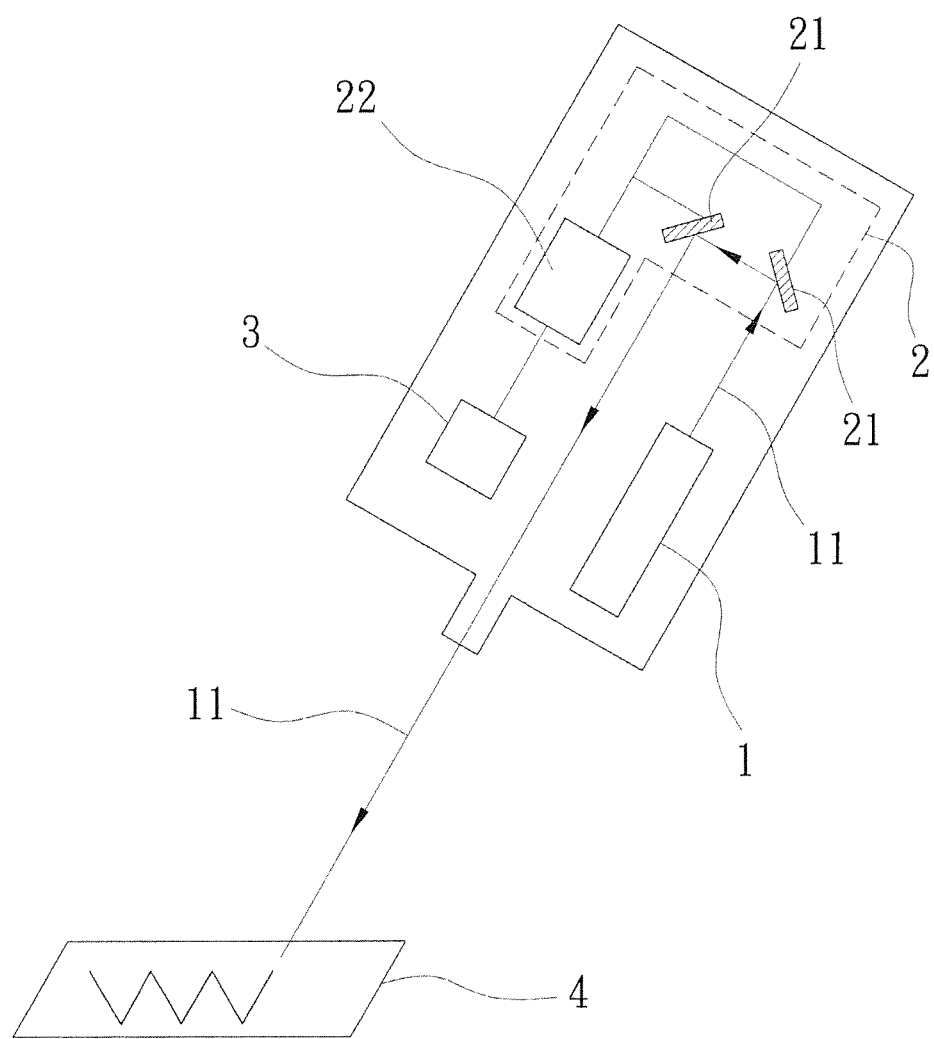

ULTRAVIOLET LASER STERILIZATION SYSTEM

BACKGROUND OF THE INVENTION

1. Field of the Invention

The present invention relates to an ultraviolet laser sterilization system, especially to an ultraviolet laser light scanner for generating and receiving ultraviolet laser light having a wavelength of 266 nm. The system takes advantage of laser collimation as well as ultraviolet-C (UV-C) sterilization for effectively achieving the efficacy of comprehensive sterilization and disinfection rapidly and flawlessly.

2. Description of Related Art

There are ubiquitous microorganisms in the living environment, e.g. air, utensils and hands. Therefore, when conducting microbiological experiments in a laboratory or hospital, researchers should make all demanded utensils used in experiments to stay in a sterile state so as not to affect the experiments and the results thereof. A sterilization technology is a process on the premise of keeping the nature of matter to destroy all microorganisms, e.g. all bacteria, spores, viruses, fungi and so on, by means of physical or chemical methods. Accordingly, a sterilization technology can effectively be used to control or inhibit the growth of a particular microorganism.

Nowadays, sterilization technologies are primarily classified into contact and non-contact types according to their uses. Contact type sterilization techniques include alcohol disinfection and chlorination methods. The alcohol disinfection method is conducted by use of alcohol with a concentration ranging from 70% to 75% or by wiping sterilization cotton moistened with alcohol across the objects. Alcohols have characteristics of being able to penetrate through the cell membrane of microorganisms and causing the internal cytoplasm to lose its metabolic functions due to complete solidification, so that the alcohol disinfection method can achieve the efficacy of sterilization. Up to now, many places, e.g. public transport, restaurants, and other public places, still take advantage of the traditional alcohol disinfection method for sterilization purposes. Although such a method has an ability of rapid sterilization without leaving pigmentation on a target object, many disadvantages still exist in the method, i.e. incomplete sterilization in some areas, reduced disinfection efficacy due to change of alcohol concentration resulting from the volatility of alcohol, time-consuming and high labor costs. The other contact sterilization technique, chlorination method, is also one of the methods commonly used in our daily life. However, recent studies have shown that chlorination is easy to make chlorine and organic reaction in the water and thus generates harmful carcinogens. Moreover, chlorine compounds are also easy to cause injury to people in use of the chlorination method for sterilization and there will be remaining chlorine left on the surface of facilities to cause surface corrosion and damage.

Non-contact sterilization techniques include ozone sterilization methods and UV-C sterilization methods. Ozone is a highly efficient, fast, and secure germicide without causing repeated pollutions. At a normal temperature and pressure, it is a pale blue gas accompanied by a natural fresh taste for not only destroying bacterial spores, viruses, fungi, botulism, Fusarium, Penicillium, *Bacillus subtilis*, natural bacteria, *Neisseria gonorrhoeae*, or the like, but also killing hepatitis A and hepatitis B viruses. However, due to the complexity of designing an ozone equipment, high designing and manufacturing cost is the main disadvantage in this method.

Currently, UV-C sterilization method is the safest and most reliable for rapid, complete and lowest hazardous sterilization without causing repeated pollutions. UV-C is now widely used in various fields, for example, UV lamp applications in medicine, is the best way to disinfection and sterilization of infectious viruses. UV lamps are conducted by sterilizing and disinfecting irradiated areas. However, limitation of UV irradiated areas is easy to cause unevenness UV brightness resulting in problems of incomplete disinfection and sterilization. Moreover, because most users think that the UV lamp will have disinfection effect as long as it has been lit, the recession problem of the UV light intensity has scarcely been valued by users. Besides, users generally determine the quality of UV lamps by the methods for assessing the quality of fluorescent lamp, i.e. assessing the light intensity of the lamp and ionization degree of the light by eyes. If the UV lamp without disinfection capability is continuously used by users, of course, it cannot effectively and thoroughly disinfect and sterilize the target object well. If people mistakenly believe that the object has been actually sterilized and further use it, it may lead to pathogenic phenomena such as infection and poisoning. In particular, the UV lamps are belong to emitted lights, so it must prohibit users from entering irradiated areas for fear of generating skin aging or cancerous lesion due to long-term exposure to UV light.

SUMMARY OF THE INVENTION

In view of the above-mentioned problems, the object of the present invention is to provide an ultraviolet laser sterilization system, especially referring to an ultraviolet laser light scanner for generating and receiving ultraviolet laser light having a wavelength of 266 nm. The system takes advantage of laser collimation as well as ultraviolet-C (UV-C) sterilization for effectively achieving the efficacy of comprehensive sterilization and disinfection rapidly and thoroughly.

Disclosed herein is an ultraviolet laser sterilization system which comprises an ultraviolet laser module and a scanning module. The ultraviolet laser module emits an ultraviolet laser light with a wavelength ranging from 200 nm to 280 nm. The scanning module includes a plurality of reflectors for receiving the ultraviolet laser light, and a controller for controlling the rotation of the reflectors to adjust an angle of emergence of the ultraviolet laser light for sterilizing a target. Therefore, by using the ultraviolet laser sterilization system, users can save much more time as well as labor costs. The present invention takes advantage of laser collimation as well as the UV-C sterilization for effectively achieving the efficacy of thorough sterilization and disinfection. Moreover, the present invention can be an adjustable sterilization system by adjusting reflectors to change the angle of emergence, which also has an advantage of complete sterilization.

According to an embodiment of the present invention, the wavelength of the ultraviolet laser light is 266 nm. The ultraviolet laser light irradiates an area ranging from 1 mm$^2$ to 4 mm$^2$ and has 5 kilowatts (KW) peak power of the light intensity.

According to an embodiment of the present invention, the system can be further provided with an ozone detector module electrically connecting to the controller. The ozone detector module is used to detect the ozone concentration in the environment, convert the ozone concentration into an electrical signal and transmit the electrical signal to the controller. The controller further adjusts the power and the irradiation time of the ultraviolet laser light on a target according to the signal.

BRIEF DESCRIPTION OF THE DRAWINGS

The FIGURE is a block diagram showing an ultraviolet laser sterilization system according to the present invention.

DETAILED DESCRIPTION OF THE PREFERRED EMBODIMENT

First, for a better understanding of the present invention, the basic concepts including laser collimation and UV-C sterilizing will be briefly described as followings. The term "laser" originated as an acronym for Light Amplification by Stimulated Emission of Radiation. Laser provides energy for active working media (gain medium) by the excitation system to amplify any photons passing through it. These photons can bounce within the laser cavity dozens to hundreds of times and finally go straight through the laser cavity to form a laser beam. Although the laser beam may disappear in the laser cavity if the forward direction of the laser beam is slightly non-parallel, the disappeared laser beam can be obtained again by fine tuning the system.

Therefore, laser beam has a better directivity, a better collimation, and the precise dosage controlling ability of the single-point fast scanning.

Furthermore, UV-C light has a wavelength of 253.7 nm, which is also generally known as a germicidal light, playing a great role in destroying the harmful bacteria, viruses, and other microorganisms. UV-C irradiation can directly cause damages to the DNA, RNA and other structures of the microorganisms leading to proteins that make up the microorganisms cannot form, so it will result in an immediate death or loss of propagation ability of the microorganisms. Generally, UV-C irradiating an object for 1-2 seconds can achieve a good result in sterilization, whereas the ozone disinfection and chlorination methods require taking several minutes or longer to achieve the same result. Accordingly, the UV-C disinfection method has been confirmed to be a disinfection and sterilization technique having many advantages of time saving, no pollution, easy operation, and lower maintenance costs.

Hereinafter, an exemplary embodiment of the present invention will be described in detail with reference to the accompanying drawings.

Referring to the FIGURE, a block diagram showing an ultraviolet laser sterilization system according to the present invention is revealed. The ultraviolet laser sterilization system comprises:

an ultraviolet laser module (1) emitting an ultraviolet laser light (11) with a wavelength ranging from 200 nm to 280 nm; and a scanning module (2) including a plurality of reflectors (21) for receiving the ultraviolet laser light (11), and a controller (22) for controlling rotation of the reflectors (21) to adjust an angle of emergence of the ultraviolet laser light (11) for sterilizing a target (4). The ultraviolet laser light (11) with a wavelength of 266 nm mainly irradiates an area ranging from 1 $mm^2$ to 4 $mm^2$ and has 5 kilowatts (KW) peak power of the light intensity.

Moreover, the system can be further provided with an ozone detector module (3) electrically connecting to the controller (22) for transmitting a signal of ozone concentration detected in the environment to the controller (22), so as to allow the controller (22) to adjust the power and the irradiation time of the ultraviolet laser light (11) on a target (4).

When assembling the abovementioned system, an ultraviolet laser module (1), a scanning module (2) comprising a plurality of reflectors (21) and a controller (22), and an ozone detector module (3) are installed to form an ultraviolet laser sterilization system having a scanner structure. This ultraviolet laser sterilization system can be an adjustable sterilization system by adjusting reflectors (21) to change the angle of emergence of the ultraviolet laser light (11), so it has an advantage of completely and rapidly sterilizing a target (4) well. The ultraviolet laser sterilization system is conducted by irradiating a target (4). After turning on the scanner, an ultraviolet laser light (11) having a wavelength ranging from 200 nm to 280 nm will be emitted from the ultraviolet laser module (1). Then the ultraviolet laser light (11) will eject from an opening of the scanner via the built-in reflector (21) of the scanning module (2) after reflection. Sterilization is conducted whenever users aim the emitted ultraviolet laser light (11) at a target (4). In addition, users can adjust an angle of emergence of the ultraviolet laser light (11) depending on their demand by a built-in controller (22) of the scanning module (2) for controlling rotation of the reflectors (21), so they can effectively control not only the laser scanning location but also a dose of the emitted ultraviolet laser light (11). The ultraviolet laser sterilization system according to the present invention can further be provided with an ozone detector module (3) for detecting an ozone concentration in the environment. The design concept is based on that ozone formed by the oxidation of oxygen atoms can penetrate into the bacteria or virus, causing DNA, RNA, and lysozyme damage and thus can effectively achieve the efficacy of sterilization. The ozone detector module (3) can transmit a signal of ozone concentration to a controller (22) by electrical connection, so as to allow the controller (22) to adjust the power and the irradiation time of the ultraviolet laser light (11) on a target (4) for thorough sterilization.

According to the above description, in comparison with the traditional technique, an ultraviolet laser sterilization system according to the present invention has the advantages as following:

1. By taking advantage of laser collimation and the single-point fast scanning of the laser light as well as a precise control of the laser light intensity, the present invention solves shortcomings, i.e. uneven brightness and unstable dosage of UV lamps, to effectively achieve the efficacy of complete sterilization and disinfection.
2. The present invention equipped with an UV-C sterilization function can effectively destroy the harmful bacteria, viruses, and other microorganisms threaten to human bodies and make them an immediate death or loss of their reproductive capacity for purpose of disinfection and sterilization.
3. With a plurality of built-in reflectors to adjust the angle of emitted ultraviolet laser light, the present invention can be made into an adjustable sterilization system having an advantage of sterilization flawlessly.
4. By an addition of an ozone detector module to detect the ozone concentration in the environment, the present invention can adjusts the power and the irradiation time of the ultraviolet laser light on a target for achieving the efficacy of fast and efficient sterilization.

What is claimed is:
1. An ultraviolet laser sterilization system comprises:
an ultraviolet laser module emitting an ultraviolet laser light with a wavelength ranging from 200 nm to 280 nm, the ultraviolet laser light irradiating an area ranging from 1 $mm^2$ to 4 $mm^2$ and having a light intensity of 5 kilowatts (KW) peak power; and
a scanning module including a plurality of reflectors for receiving the ultraviolet laser light, and a controller for controlling rotation of the reflectors to adjust an angle of emergence of the ultraviolet laser light for sterilizing a target.

2. The ultraviolet laser sterilization system as claimed in claim 1, wherein the wavelength of the ultraviolet laser light is 266 nm.

3. The ultraviolet laser sterilization system as claimed in claim 1, wherein the system is further provided with an ozone detector module electrically connecting to the controller for transmitting a signal of ozone concentration detected in the environment to the controller, so as to allow the controller to adjust the power and the irradiation time of the ultraviolet laser light on a target.

\* \* \* \* \*